2
United States Patent [19]

Tuttle

[11] 4,425,336
[45] Jan. 10, 1984

[54] 3,4-DIHYDROXY-N-[3-(4-DIHYDROXY-PHENYL)-1-METHYL-N-PROPYL]-BETA-PHENETHYLAMINE CYCLODEXTRIN COMPLEXES

[75] Inventor: Ronald R. Tuttle, Plantation, Fla.

[73] Assignee: Key Pharmaceuticals, Inc., Miami, Fla.

[21] Appl. No.: 381,567

[22] Filed: May 24, 1982

[51] Int. Cl.³ .................. A61K 31/73; C08B 37/16
[52] U.S. Cl. ................................. 424/180; 536/46
[58] Field of Search ..................... 536/46; 424/180

[56] References Cited

U.S. PATENT DOCUMENTS 3,987,200  10/1976  Tuttle et al. ................ 424/330
4,228,160  10/1980  Szejtli et al. ................ 424/180

*Primary Examiner*—Johnnie R. Brown
*Assistant Examiner*—Elli Peseler
*Attorney, Agent, or Firm*—Wegner & Bretschneider

[57] ABSTRACT

Cardiac contractility agents are provided which are 3,4-dihydroxy-N-[3-(4-hydroxyphenyl)-1-methyl-n-propyl]-beta-phenethylamine cyclodextrin complexes.

3 Claims, No Drawings

3,4-DIHYDROXY-N-[3-(4-DIHYDROXYPHENYL)-1-METHYL-N-PROPYL]-BETA-PHENETHYLAMINE CYCLODEXTRIN COMPLEXES

BACKGROUND OF THE INVENTION

The present invention provides an improved form of the compound 3,4-dihydroxy-N-[3-(4-hydroxyphenyl)-1-methyl-n-propyl]-beta-phenethylamine, which is an intravenously administered agent for increasing cardiac contractility. It is not marketed orally in view of impractically large dosage that would be needed for 3,4-dihydroxy-N-[3-(4-hydroxyphenyl)-1-methyl-n-propyl]-beta-phenethylamine for oral administration. 3,4-dihydroxy-N-[3-(4-hydroxyphenyl)-1-methyl-n-propyl]-beta-phenethylamine is disclosed in Tuttle et al., U.S. Pat. No. 3,987,200, granted Oct. 19, 1976, and entitled Method for Increasing Cardiac Contractility. The present invention provides a complex of 3,4-dihydroxy-N-[3-(4-hydroxyphenyl)-1-methyl-n-propyl]-beta-phenethylamine with cyclodextrin. Cyclodextrins have been known in the art for many years prior to the invention described in the Tuttle et al. patent, for example, Cohen et al., "Interaction of Pharmaceuticals with Schardinger Dextrins I", *Journal of Pharmaceutical Sciences*, Vol. 52, pp. 132–136 (1963).

SUMMARY OF THE INVENTION

In accordance with a first aspect of the present invention there is provided a novel complex of 3,4-dihydroxy-N-[3-(4-hydroxyphenyl)-1-methyl-n-propyl]-beta-phenethylamine wherein the 3,4-dihydroxy-N-[3-(4-hydroxyphenyl)-1-methyl-n-propyl]-beta-phenethylamine is complexed with a cyclodextrin, the cyclodextrin in a preferred embodiment being beta-cyclodextrin, and in a still further embodiment having about two molecules of beta-cyclodextrin complexed to one molecule of 3,4-dihydroxy-N-[3-(4-hydroxyphenyl)-1-methyl-n-propyl]-beta-phenethylamine.

In accordance with a second aspect of the present invention, oral dosage unit forms, preferably tablets, are provided of the novel complex of the present invention. Unlike the known compound dobutamine which has proven effective as a cardiac contractility agent in intravenous form, the present complex has an improved level of effectiveness which permits its administration to animals via the oral route.

In accordance with a further aspect of the invention rectal, sublingual and buccal forms are contemplated.

In accordance with a further aspect of the present invention there is provided a method for increasing cardiac tractility in a warm-blooded animal suffering from depressed cardiac tractility which comprises the administration of a pharmaceutically effective amount of a complex of 3,4-dihydroxy-N-[3-(4-hydroxyphenyl)-1-methyl-n-propyl]-beta-phenethylamine and cyclodextrin to the animal.

DETAILED DESCRIPTION OF THE INVENTION

The complex of the present invention may be applied orally or in other conventional dosage forms, including orally, subligually and rectally. In the prior art there has been a successful use of 3,4-dihydroxy-N-[3-(4-hydroxyphenyl)-1-methyl-n-propyl]-beta-phenethylamine intravenously, which route of administration was required as a practical matter due to the high dosage that is required for 3,4-dihydroxy-N-[3-(4-hydroxyphenyl)-1-methyl-n-propyl]-beta-phenethylamine. With the increased efficacy of the complex of the present invention it is possible to utilize the oral, sublingual and rectal dosage forms. As a pharmaceutically effective amount may be mentioned from about 10 to about 150 milligram per killogram body weight per day for an oral dosage unit form, and still more preferably about 50 mg/kg/day. Dosage unit form for oral administration include the conventional dosage formulations for pharmaceuticals, with tablets being particularly suitable. Although excipients may generally be added to the active ingredient in the formulation of tablets, it is unnecessary to do so in the present invention. For examples, tablets of about 1.5 gram consisting entirely of the active complex may be manufactured through conventional tableting techniques, the patient taking several of these tablets at one time on a once a day basis in accordance with a preferred aspect of the present invention. Sublingual dosage forms are preferably prepared in the form of a wafer and suppository forms are prepared by compounding the complex with a conventional wax.

The following examples illustrate the invention:

1 gm beta-cyclodextrin was dissolved in 10 ml water at a temperature of 58° C. To this solution 0.135 g 3,4-dihydroxy-N-[3-(4-hydroxyphenyl)-1-methyl-n-propyl]-beta-phenethylamine dissolved in 2 ml ethanol (95%) was added dropwise. While stirring, the solution was left to cool slowly for about 4.5 hours to room temperature. The crystals were separated during this cooling period and the suspension was thereafter left overnight at 5° C. First the crystals were collected by filtration and washed twice with ethanol (5 ml, 95%) to remove the excess 3,4-dihydroxy-N-[3-(4-hydroxyphenyl)-1-methyl-n-propyl]-beta-phenethylamine. Then they were dried over phosphorus pentoxide to yield 1.05 g of the product. 3,4-dihydroxy-N-[3-(4-hydroxyphenyl)-1-methyl-n-propyl]-beta-phenethylamine content was measured by spectrophotometry at 280 nm and found to be 10.2% and 10.24%. This indicates that the complex contains two beta-cyclodextrin molecules per one molecule 3,4-dihydroxy-N-[3-(4-hydroxyphenyl)-1-methyl-n-propyl]-beta-phenethylamine. The 3,4-dihydroxy-N-[3-(4-hydroxyphenyl)-1-methyl-n-propyl]-beta-phenethylamine may be prepared through the following procedure: In a stainless steel hydrogenation bottle were placed 17.6 g (0.1 mol) of 4-(p-methoxyphenyl)-3-buten-2-one, 80 ml of ethyl acetate, and 1 g of Raney nickel catalyst. The hydrogenation bottle was attached to a Paar low pressure hydrogenation apparatus and the solution was hydrogenated under an initial hydrogen pressure of 50 psi. The hydrogenation was carried out at room temperature and after about 12 hours one equivalent of hydrogen had been absorbed. The catalyst was filtered from the reduction mixture and 18.1 g (0.1 mol) of homoveratrylamine were added to the reduction mixture. To the reduction mixture was then added 3.5 g of 5 percent palladium on carbon catalyst and the mixture was hydrogenated under a hydrogen pressure of 50 psi. at room temperature for 12 hours. The catalyst was removed by filtration and the filtrate was evaporated to a small volume yielding the compound 3,4-dihydroxy-N-[3-(4-hydroxyphenyl)-1-methyl-n-propyl]-beta-phenethylamine. Clinically instrumented mongrel dogs were measured for pressure in the left ventricle of the heart for both 3,4-dihydroxy-N-[3-(4-hydroxyphenyl)-1-methyl-n-propyl]-beta-phenethylamine hydrochloride of Tuttle et al. and the instant beta-cyclodextrin with the following results:

| Test | Compound | Response |
|------|----------|----------|
| 1 | 3,4-dihydroxy-N—[3-(4-hydroxyphenyl)-1-methyl-n-propyl]-beta-phenethylamine hydrochloride | 0 |
| 2 | 3,4-dihydroxy-N—[3-(4-hydroxyphenyl)-1-methyl-n-propyl]-beta-phenethylamine hydrochloride | + |
| 3 | 3,4-dihydroxy-N—[3-(4-hydroxyphenyl)-1-methyl-n-propyl]-beta-phenethylamine hydrochloride | 0 |
| 4 | 3,4-dihydroxy-N—[3-(4-hydroxyphenyl)-1-methyl-n-propyl]-beta-phenethylamine beta-cyclodextrin | +++ |
| 5 | 3,4-dihydroxy-N—[3-(4-hydroxyphenyl)-1-methyl-n-propyl]-beta-phenethylamine beta-cyclodextrin | +++ |
| 6 | 3,4-dihydroxy-N—[3-(4-hydroxyphenyl)-1-methyl-n-propyl]-beta-phenethylamine beta-cyclodextrin | +++ |
| 7 | 3,4-dihydroxy-N—[3-(4-hydroxyphenyl)-1-methyl-n-propyl]-beta-phenethylamine beta-cyclodextrin | ++ |
| 8 | 3,4-dihydroxy-N—[3-(4-hydroxyphenyl)-1-methyl-n-propyl]-beta-phenethylamine beta-cyclodextrin | ++ |

In each of the eight trials above, an identical amount of the compound of each test was used (5 gm). The code for the response strength is as follows:

+++: large response
++: medium response
+: small response
0: no response.

What is claimed is:

1. A complex of 3,4-di-hydroxy-N-[3-(4-hydroxyphenyl)-1-methyl-n-propyl]-beta-phenethylamine and at least one mole cyclodextrin per mol 3,4-di-hydroxy-N-[3-(4-hydroxyphenyl)-1-methyl-n-propyl]-beta-phenethylamine.

2. A complex of claim 1 wherein the cyclodextrin is in the beta form.

3. A complex of claim 1 or 2 wherein about two molecules of cyclodextrin are present per molecule of 3,4-dihydroxy-N-[3-(4-hydroxyphenyl)-1-methyl-n-propyl]-beta-phenethylamine.

* * * * *